(12) United States Patent
Spiers et al.

(10) Patent No.: US 11,401,388 B2
(45) Date of Patent: Aug. 2, 2022

(54) PROCESS OF FORMING AN ACID-DOPED POLYANILINE SOLUTION

(71) Applicants: Massachusetts Institute of Technology, Cambridge, MA (US); Swinburne University of Technology, Hawthorn (AU)

(72) Inventors: Maryanne Spiers, Hawthorn (AU); Daniel Eldridge, Hawthorn (AU); Peter Kingshott, Aarhus (DK); David Nielsen, Fishermans Bend (AU); Karl Pavey, Fishermans Bend (AU); Yen Truong, Clayton (AU); Gregory Rutledge, Cambridge, MA (US)

(73) Assignees: Massachusetts Institute of Technology, Cambridge, MA (US); Swinburne UIniversity of Technolooy, Hawthorn (AU)

( * ) Notice: Subject to any disclaimer, the term of this patent is extended or adjusted under 35 U.S.C. 154(b) by 249 days.

(21) Appl. No.: 16/740,628

(22) Filed: Jan. 13, 2020

(65) Prior Publication Data

US 2020/0223990 A1  Jul. 16, 2020

Related U.S. Application Data

(60) Provisional application No. 62/792,071, filed on Jan. 14, 2019.

(51) Int. Cl.
*C08J 3/21* (2006.01)
*G01N 21/78* (2006.01)
(Continued)

(52) U.S. Cl.
CPC ............. *C08J 3/212* (2013.01); *C08K 5/42* (2013.01); *D01D 5/0038* (2013.01); *D01F 6/76* (2013.01);
(Continued)

(58) Field of Classification Search
CPC ..... C08J 3/212; C08J 2379/02; G01N 21/783; C08K 5/42; D01D 5/0038; D04H 3/009; D01F 6/76
See application file for complete search history.

(56) References Cited

U.S. PATENT DOCUMENTS 5,135,682 A * 8/1992 Cohen ............ D01F 6/76
106/311
6,429,282 B1 * 8/2002 Wang ............ H01B 1/128
252/500

(Continued)

OTHER PUBLICATIONS

Maryann Spiers at al.; Poster entitled "High Concentration (+)-Camphor-10-Sulfonic Acid Doped Polyaniline Electrospun Nanofibers"; presented Jan. 16, 2018 at the Electrospin Conference.
(Continued)

*Primary Examiner* — Cephia D Toomer
(74) *Attorney, Agent, or Firm* — Stevens & Showalter LLP (57) ABSTRACT

A method of forming an acid-doped polyaniline (emeraldine salt) (PANi-ES) solution including steps of: (i) mixing polyaniline (emeraldine base) (PANi-EB) with a PANi-EB solvent and a gel-inhibitor to form a gel-inhibited PANi-EB solution; (ii) removing the gel-inhibitor from the gel-inhibited PANi-EB solution to form a PANi-EB solution; and (iii) adding an acid dopant to the PANi-EB solution to form a PANi-ES solution.

12 Claims, 9 Drawing Sheets

(51) Int. Cl.
*C08K 5/42* (2006.01)
*D01D 5/00* (2006.01)
*D04H 3/009* (2012.01)
*D01F 6/76* (2006.01)

(52) U.S. Cl.
CPC .......... *D04H 3/009* (2013.01); *G01N 21/783* (2013.01); *C08J 2379/02* (2013.01)

(56) References Cited

U.S. PATENT DOCUMENTS

| | | | |
|---|---|---|---|
| 10,265,662 B2 * | 4/2019 | Hoek | ................. C08K 5/17 |
| 2011/0240556 A1 * | 10/2011 | Hoek | ................. C08G 73/0266 |
| | | | 210/500.21 |

OTHER PUBLICATIONS

Maryann Spiers at al; "Novel Method for the Dissolution of High Concentration, High Molecular Weight Acid Doped Polyaniline for Processing into Novel Electrospun Nanofibers"; presented May 2018 at the Swinburne Research Conference.

Information pertaining to Public Disclosure set forth in the IDS Cover Letter submitted together with an Information Disclosure Statement dated Sep. 21, 2020, 2 pages.

* cited by examiner

PROCESS OF FORMING AN ACID-DOPED POLYANILINE SOLUTION

CROSS REFERENCE TO RELATED APPLICATION

This application claims the benefit of U.S. Provisional Patent Application No. 62/792,071, filed Jan. 14, 2019 and entitled "A PROCESS OF FORMING AN ACID-DOPED POLYANILINE SOLUTION", the entire disclosure of which is incorporated herein by reference.

FIELD OF INVENTION

The present invention relates to a process of forming an acid-doped polyaniline solution. The present invention also relates to a process of forming a fibre using an acid-doped polyaniline solution.

BACKGROUND OF THE INVENTION

Polyaniline, in both its semi-conductive emeraldine base form (PANi-EB) and conductive emeraldine salt form (PANi-ES), is widely considered to be intractable and unsuitable for solution processing. While boasting significant environmental stability and conductivity, its applications have been drastically limited by a tendency to aggregate in solution. Self-association through the electrostatic attraction of oppositely charged imine and amine sites on the polyaniline polymer backbone has previously been identified as the cause of this aggregation. As such, it is difficult to produce polyaniline solutions for materials such as acid-doped polyaniline (PANi-ES) fibres, which have potential applications ranging from filtration to chemical sensing.

Figure 1:
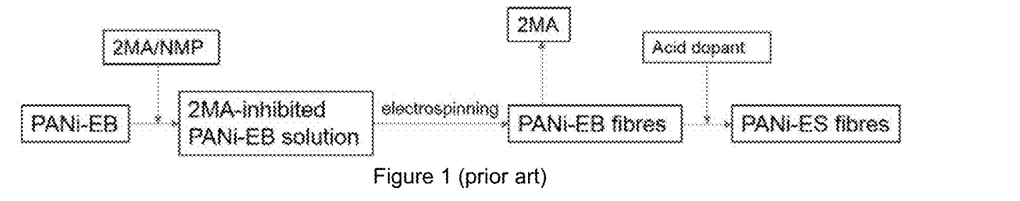
FIG. 1 is schematic illustrating a prior art method of forming a PANi-ES fibre involving heterogenous acid doping of a PANi-EB fibre.

Currently, (+)-camphor-10-sulfonic acid doped polyaniline fibres (PANi-HCSA) are formed by dissolving PANi-EB using a gel inhibitor 2-methylaziridine (2MA) in N-Methyl-2-pyrrolidone (NMP). 2MA interacts preferentially with the imine site on the PANi-EB to inhibit chain association and cross-linking. This allows the formation of a gel-inhibited PANi-EB solution which is then wet electrospun to remove the 2MA and form microscale PANi-EB fibres. The fibres are subsequently doped using aqueous hydrochloric acid (HCl) or 2-Acrylamido-2-methylpropane sulfonic acid (AMPSA) to form PANi-HCSA fibres (see FIG. 1).

However, there are a number of disadvantages with this process. For example, 2MA has a low flash point (−10° C.) which makes fibre formation risky because electrospinning conductive polymers can result in the production of electrical sparks, which might cause 2MA and NMP (a flammable solvent) to ignite. 2MA is also highly toxic which increases the Occupational Health & Safety (OH&S) risks for an operator.

Morpholine has also been used as a gel inhibitor. However, it has been reported that morpholine has several undesirable effects including a reduction in conductivity and degradation of the resulting polymers. In one example, it was reported that thermally annealed PANi-EB films produced by a morpholine/NMP solvent system exhibited poor conductivity (Chien-Chung Han and Rong-Chyuan Jeng, Chem. Commun. 1997, pages 553-554).

Accordingly, it is desirable to provide a safer and simpler method of forming PANi-ES fibres.

SUMMARY OF THE INVENTION

In a first aspect, the present invention provides a method of forming an acid-doped polyaniline (emeraldine salt) (PANi-ES) solution including steps of:

(i) mixing polyaniline (emeraldine base) (PANi-EB) with a PANi-EB solvent and a gel-inhibitor to form a gel-inhibited PANi-EB solution;

(ii) removing the gel-inhibitor from the gel-inhibited PANi-EB solution to form a PANi-EB solution; and (iii) adding an acid dopant to the PANi-EB solution to form a PANi-ES solution.

In a second aspect, the present invention provides an acid-doped solution comprising at least 0.01 wt % PANi-ES solubilized in a polar aprotic solvent prepared by the method of the first aspect of the invention.

In a third aspect, the present invention provides a method of forming a PANi-ES fibre from a solution comprising at least 0.01 wt % PANi-ES, said method including electrospinning the PANi-ES solution to form the PANi-ES fibre.

In a fourth aspect, the present invention provides a PANi-ES fibre having an average diameter of less than 10 μm formed from electrospinning a PANi-ES solution.

In a fifth aspect, the present invention provides a fabric or membrane comprising a PANi-ES fibre prepared by the methods of the invention.

In sixth aspect, the present invention provides a gas sensor for testing the presence of a gaseous substance, said gas sensor including a fabric or membrane of the fifth aspect of the invention.

DETAILED DESCRIPTION

The present invention is predicated at least in part on the realisation that reagents previously thought to be unsuitable candidates as gel-inhibitors when paired with an appropriate PANi-EB solvent, can facilitate formation of a PANi-ES solution having a concentration of at least 0.01 wt % PANi-ES and the gel-inhibitor may be removed before acid doping to provide a PANi-ES solution without inducing cross-linking or degradation of the polymer and that is suitable for use in preparing polyaniline products such as acid doped polyaniline fibres.

In a first aspect, the present invention provides a method of forming an acid-doped polyaniline (emeraldine salt) (PANi-ES) solution including steps of:

(i) mixing polyaniline (emeraldine base) (PANi-EB) with a PANi-EB solvent and a gel-inhibitor to form a gel-inhibited PANi-EB solution;

(ii) removing the gel-inhibitor from the gel-inhibited PANi-EB solution to form a PANi-EB solution; and (iii) adding an acid dopant to the PANi-EB solution to form a PANi-ES solution.

The method of the present invention is directed towards preparing solutions of the emeraldine form of polyaniline $(([C_6H_4NH]_2[C_6H_4N]_2)_n)$. More specifically, the method of the present invention is directed towards preparing solutions of polyaniline in its semi-conductive emeraldine base form (PANi-EB) and conductive emeraldine salt form (PANi-ES).

In some embodiments, the PANi-EB has a molecular weight of greater than 50,000 Da (g/mol), preferably ranging from 65,000-100,000 Da (g/mol).

As used herein, the term "PANi-EB solvent" refers to a solvent capable of solubilizing at least a portion of the PANi-EB. For example, the solvent may solubilize the PANi-EB in an amount of 0.1 wt % or less. At least a portion of the PANi-EB may be suspended in the solvent. In some embodiments, at least a portion of the gel inhibitor is solubilized in the solvent. In some embodiments, at least a portion of the gel inhibitor is suspended in the solvent.

In some embodiments, the PANi-EB solvent is an aprotic solvent, preferably a polar aprotic solvent, more preferably a dipolar aprotic solvent. Suitable examples of solvents include dimethylformamide (DMF), dimethylacetamide (DMAC), N-methyl-2-pyrrolidone (NMP), 2-methylanisole, N-ethyl-2-pyrrolidinone, 1-cyclohexyl-2-pyrrolidinone, 1-methyl-2-piperidone, n-methylcaprolactam, 1,5-dimethyl-2-pyrrolidinone, 2-pyrrolidinone, 1,3-dimethyl-2-imidazolidinone, 1,3-dimethyl-3,4,5,6-tetrahydro-2(H)-pyrimidinone, 1-methyl-2-pyridone, 1-acetylpyrrolidine, 1-acetylpiperidine, 1-acetyl-3-methylpiperidine, N,N-dimethylpropionamide or dimethyl sulfoxide (DMSO), or mixtures thereof. In particular embodiments, the solvent is selected from dimethylformamide, dimethylacetamide, N-methyl-2-pyrrolidone and dimethyl sulfoxide.

In some embodiments, the PANi-EB and gel inhibitor are mixed to provide contact between the PANi-EB and gel inhibitor.

In some embodiments, the gel inhibitor has a basic pH. Suitably, the gel inhibitor is an amine. More suitably, the gel inhibitor is a secondary amine. In some embodiments, the gel inhibitor is selected from morpholine, 2-methylaziridine, azetidine, pyrrolidine, piperidine, hexamethyleneimine, heptamethyleneimine, indoline, thiomorpholine, 2,6-dimethylmorpholine, diethylamine, dicyclohexylamine, dipropylamine, dibutylamine, N-methylhexylamine, 3,3-dimethylpiperidine, 3,5-dimethylpiperidine, and mixtures thereof. In particular embodiments, the gel inhibitor is morpholine.

In some embodiments, the gel-inhibitor has a lower boiling point to the PANi-EB solvent such that the gel-inhibitor and PANi-EB solvent have a difference in boiling points ranging from 5-50° C., preferably 20-50° C., more preferably 20-40° C.

In some embodiments, the acid dopant is an organic acid, preferably an organic sulfonic acid such as (+)-camphor-10-sulfonic acid (HCSA), p-toluenesulfonic acid (p-TSA), dinonylnaphthalenedisulfonic acid, or dodecylbenzenesulfonic acid (DBSA). More preferably, the acid dopant is (+)-camphor-10-sulfonic acid (HCSA).

In some embodiments, the acid dopant is an inorganic acid such as hydrochloric acid, hydrobromic acid, sulfuric acid or nitric acid.

In some embodiments, step (i) includes mixing polyaniline (emeraldine base) (PANi-EB) with a PANi-EB solvent and a gel-inhibitor to form a gel-inhibited PANi-EB solution having a concentration of at least 0.01 wt %, preferably at least 0.1 wt %, more preferably ranging from 1-50 wt %, even more preferably 5-40 wt %, yet even more preferably 10-30 wt %, most preferably 12-16 wt % PANi-EB.

In some embodiments, step (i) includes mixing PANi-EB with a PANi-EB solvent and a gel-inhibitor such that the gel-inhibitor to PANi-EB solvent ratio ranges from 1:1 to 1:20. Suitably, the gel-inhibitor to PANi-EB solvent ratio is about 1:10, more especially about 1:5.

In some embodiments, step (i) includes a step of adding a carrier polymer.

In some embodiments, the carrier polymer has a molecular weight of at least 100,000 Da (g/mol), preferably, at least 200,000 Da (g/mol), more preferably, at least 300,000 Da (g/mol).

In some embodiments, the carrier polymer is polyethylene oxide.

In some embodiments, step (i) includes a step of adding a carrier polymer such that the gel-inhibited PANi-EB solution has a concentration of up to 3 wt %, preferably up to 1 wt %, more preferably up to 0.5 wt %, even more preferably up to 0.1 wt % of carrier polymer.

In some embodiments, step (ii) includes removing the gel-inhibitor from the gel-inhibited PANi-EB solution by distillation. The distillation may be performed in the presence or absence of heat and at atmospheric, reduced or elevated pressure. Most suitably, the gel inhibitor is removed by vacuum distillation.

In some embodiments, the PANi-EB solution is a homogeneous PANi-EB solution.

In some embodiments, step (iii) includes adding an acid dopant to the PANi-EB solution such that the molecular ratio of PANi-EB to acid dopant ranges from 2:1 to 1:4, preferably about 1:2.

In some embodiments, the PANi-ES solution formed has a concentration ranging from 0.01-50 wt %, preferably ranging from 1-30 wt %, more preferably 5-20 wt %, even more preferably 12-16 wt % PANi-ES.

In some embodiments, as measured by a 2-point probe method, the PANi-ES formed has a conductivity of at least 0.0001 $Scm^{-1}$, preferably a conductivity of at least 0.001 $Scm^{-1}$, more preferably a conductivity ranging from 0.001-1 $Scm^{-1}$.

In some embodiments, the method includes a step of adding an organic solvent to the PANi-ES solution, preferably after step (iii).

In some embodiments, the method includes a step of replacing at least part of the PANi-EB solvent with an organic solvent.

In some embodiments, the method includes a step of adding an organic solvent to the PANi-ES solution such that the PANi-EB solvent to organic solvent ratio ranges from 1:5 to 5:1. In some embodiments, the organic solvent has a boiling point lower than the boiling point of the PANi-EB solvent. In some embodiments, the boiling point of the organic solvent is less than 150° C., preferably less than 140° C., more preferably less than 130° C., even more preferably less than 120° C.

In some embodiments, the organic solvent is chlorinated. Suitably, the organic solvent can be selected from the following list of examples: dichloromethane (DCM), 1,1,2,2-tetrachloroethane (TCM), dichlorobenzene (DCB) or chlorobenzene (CB).

In a particular embodiment of the invention, (+)-camphor-10-sulfonic acid doped polyaniline fibres (PANi-HCSA) are formed by the method of the invention wherein the gel inhibitor is morpholine, the solvent is dimethylformamide and the acid dopant is (+)-camphor-10-sulfonic acid.

In a second aspect, the present invention provides an acid-doped solution comprising at least 0.01 wt % PANi-ES solubilized in a polar aprotic solvent prepared by the method of the first aspect of the invention.

In a third aspect, the present invention provides a method of forming a PANi-ES fibre from a PANi-ES solution comprising at least 0.01 wt % PANi-ES, said method including electrospinning the PANi-ES solution to form the PANi-ES fibre.

In some embodiments, the PANi-ES solution comprises a chlorinated organic solvent. In some embodiments, the chlorinated solvent is selected from dichloromethane (DCM), 1,1,2,2-tetrachloroethane (TCM) or chlorobenzene (CB).

In some embodiments, the method includes dry electrospinning a PANi-ES solution to form the PANi-ES fibre. In one particular embodiment, the method includes using a single-nozzle dry electrospinning process to form the PANi-ES fibre. Advantageously, the electrospinning method does not require a coagulation bath.

In some embodiments, the method includes co-axial electrospinning a PANi-ES solution to form the PANi-ES fibre.

In some embodiments, the PANi-ES fibre formed has an average diameter of less than 10 μm, preferably less than 1 μm, more preferably 70-1,000 nm, even more preferably 100-900 nm, yet even more preferably 400-600 nm, still even more preferably about 450 nm.

In a fourth aspect, the present invention provides a PANi-ES fibre having an average diameter of less than 10 μm formed from electrospinning a PANi-ES solution prepared by the method of the third aspect.

In a fifth aspect, the present invention provides a fabric or membrane comprising a PANi-ES fibre according to the fourth aspect of the invention.

In some embodiments, the fabric or membrane is woven or non-woven. Preferably, the fabric or membrane may be a non-woven fabric, for example, a non-woven fabric mat.

In a sixth aspect, the present invention provides a gas sensor for testing for the presence of a target substance, said gas sensor including a fabric or membrane comprising a PANi-ES fibre as a sensing element formed by any one of the previously described methods.

In some embodiments, the fabric or membrane may change in appearance in the presence of a target gas. Suitably, the change in appearance is a change in colour of the fabric or membrane.

In some embodiments, the fabric or membrane is a non-woven fibre fabric mat.

In some embodiments, the fabric or membrane may function as a transducer by exhibiting a change in resistance, impedance, or some other electrical property in the presence of a target substance. Suitably, the electrical change may be interrogated by inducing the flow of electrons due to a change in conductivity or resistance of the fabric or membrane.

In some embodiments, the gas sensor is configured to detect a redox active gas. Suitably, the redox active gas is a nitrogen-containing gas. More suitably, the gas sensor is configured to detect an amine or an imine-containing molecule. Even more suitably, the gas sensor is configured to detect ammonia. Suitably, the gas sensor is configured to detect a minimum concentration of 1 ppm of ammonia. More suitably, the gas sensor is configured to detect a concentration ranging from 1-1,000 ppm of ammonia.

Preferred embodiments of the present invention are hereinafter described by way of example only, with reference to the accompanying drawings.

Figure 2:
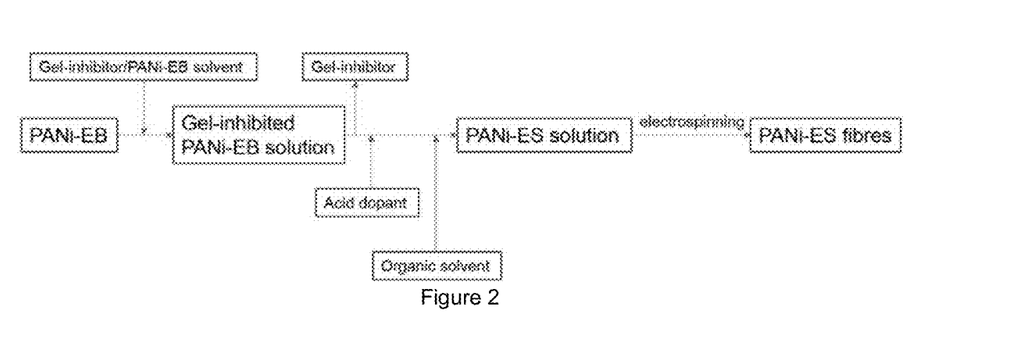
FIG. 2 is schematic illustrating an embodiment of the present invention of forming a PANi-ES fibre.

FIG. 2 illustrates a method of forming PANi-ES fibres from PANi-EB that embraces the first to fourth aspects of the invention. The method forms (1) a gel-inhibited PANi-EB solution that is heat treatable to remove the gel-inhibitor, (2) a PANi-ES solution and (3) PANi-ES fibres by electrospinning the PANi-ES solution.

Formation of Gel-Inhibited PANi-EB Solution

Figure 3:
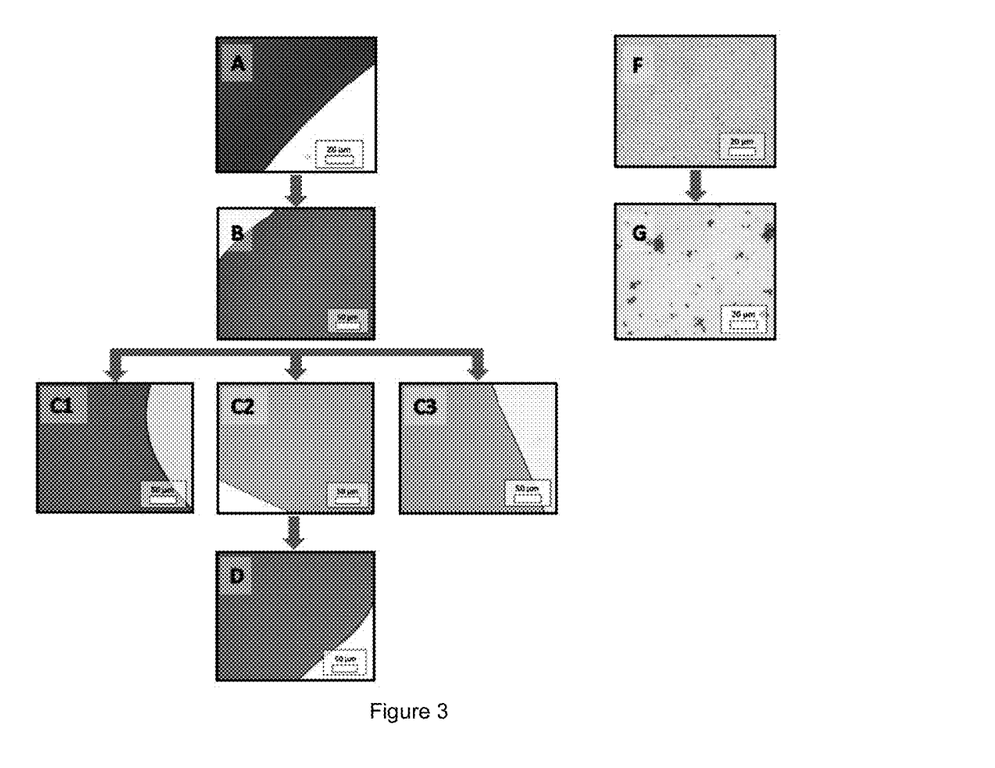
FIG. 3 provides optical microscope images assessing the solubility of A) 20% PANi-EB in 1:1 DMF/morpholine, B) 15% PANi-EB in DMF after complete morpholine distillation, C1) 13% PANi-HCSA in 3:1 DMF/CB with incomplete morpholine distillation, C2) 13% PANi-HCSA in 3:1 DMF/CB with complete morpholine distillation, C3) 16% PANi-HCSA in DMF after complete morpholine distillation D) 13% PANi-HCSA in a 3:1 DMF/chlorobenzene after two weeks of shelf storage, E) 1% PANi-EB in DMF, and F) 1% PANi-HCSA in DMF.

PANi-EB was mixed with a gel-inhibitor (e.g. morpholine) and a PANi-EB solvent (e.g. DMF) to form a gel-inhibited PANi-EB solution. The dissolution of PANi-EB is based on the "gel inhibition" mechanism in which morpholine is used to preferentially interact with imine site of the polymer backbone, rendering it inaccessible for self-association (see FIG. 3). A carrier polymer (e.g. polyethylene oxide) can be added to reduce the brittleness of the fibre that is ultimately produced from the PANi-ES solution.

Distillation

This gel-inhibited PANi-EB solution is then distilled to remove the gel-inhibitor before the acid dopant (e.g. HCSA) is added to the solution to form a PANi-ES solution (e.g. PANi-HCSA). This minimises any acid-base interactions between the basic gel inhibitor and acidic dopant.

The distillation takes advantage of the boiling point difference between the gel-inhibitor and PANi-EB solvent to facilitate removal of the gel-inhibitor from the gel-inhibited PANi-EB solution by distillation, with or without the application of heat to form a PANi-ES solution.

Distillation was not previously considered a viable processing method for PANi-EB solutions due to PANi-EB's known propensity to thermally decompose. Specifically, PANi-EB is known to undergo cross-linking at imine sites when heated in solution, which produces an insoluble brown precipitate that cannot be doped. The present invention produces a PANi-EB that is chemically stable at temperatures below 140° C. for a period of 30-60 minutes.

Acid Doping

The PANi-EB solution was replenished with an organic solvent (e.g. chlorobenzene) to produce a PANi-EB solvent/organic solvent mixture. An acid dopant (e.g. HCSA) was added to the PANi-EB solution to form a PANi-ES solution (e.g. PANi-HCSA solution).

It is believed that acid doping of PANi-EB increases the total number of charge carrying delocalized electrons along the polymer backbone. Literature on polyaniline proposes that the polymer is deprotonated by an alkaline vapour via an acid (dopant)-based (vapour) reaction, it reduces the number of charge carriers along the polymer backbone. This results in a reduction in conductivity.

The low boiling point of the chlorinated organic solvent facilitates evaporation of the solvent mixture during electrospinning and other processes and enables the formation of a PANi-ES fibre having an average diameter of less than 1,000 nm.

Figure 6:
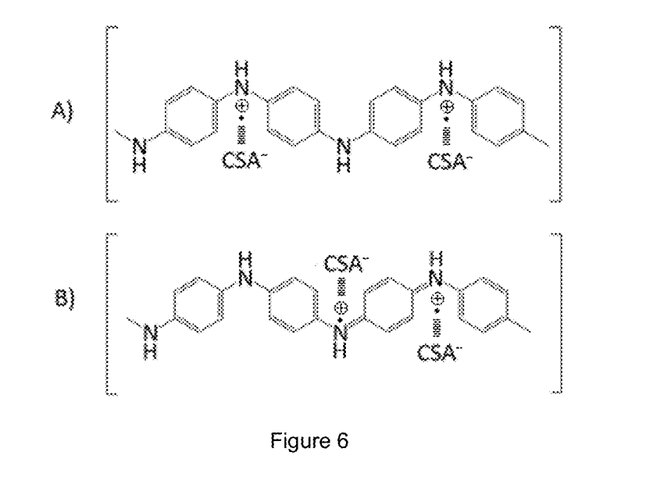
FIG. 6 illustrates the structure of PANi-HCSA in its highly conductive polaron form (structure A) and its less conductive bipolaron form (structure B).
Figure 7:
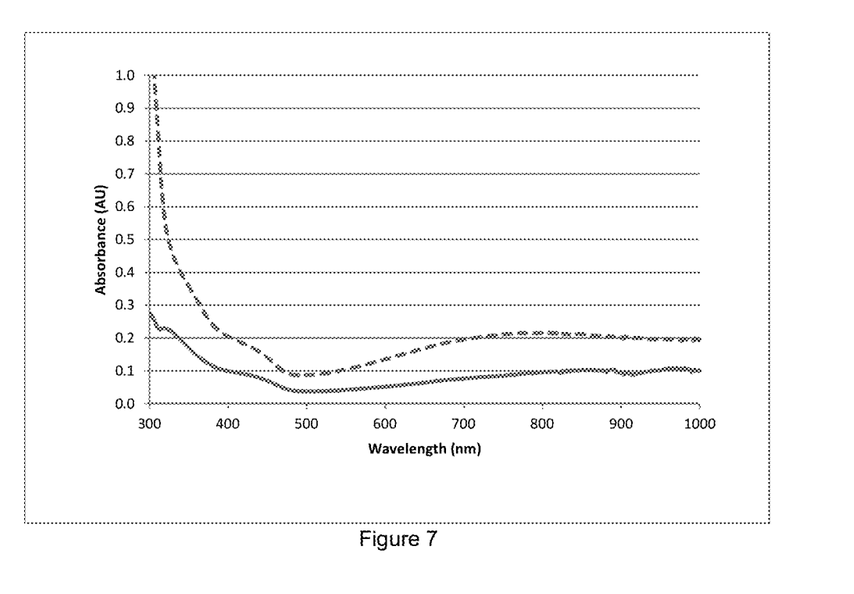
FIG. 7 provides the UV-visible spectra of 1 wt % PANi-HCSA in DMF (broken line) and 0.25 wt % PANi-HCSA in 2:1 TCE/DMF (solid line) after processing with the novel morpholine distillation step.
Figure 8:
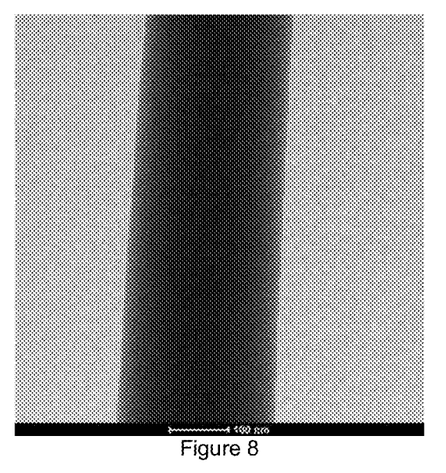
FIG. 8 is a TEM image of 99.7 wt % PANi-HCSA fibres with 0.3 wt % PEO, which demonstrate homogenous blending and absence of any undissolved or cross-linked aggregate.
Figure 9:
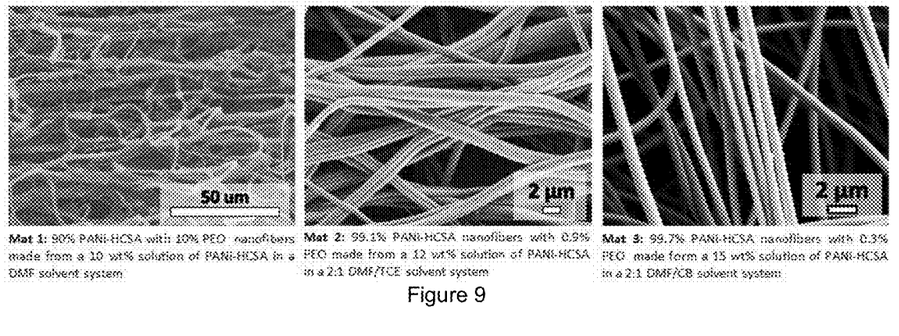
FIG. 9 provides SEM images illustrating the results of various blends of PANi-HCSA and PEO and solvent systems that were optimised to produce nanoscale fibres of good morphology.
Figure 10:
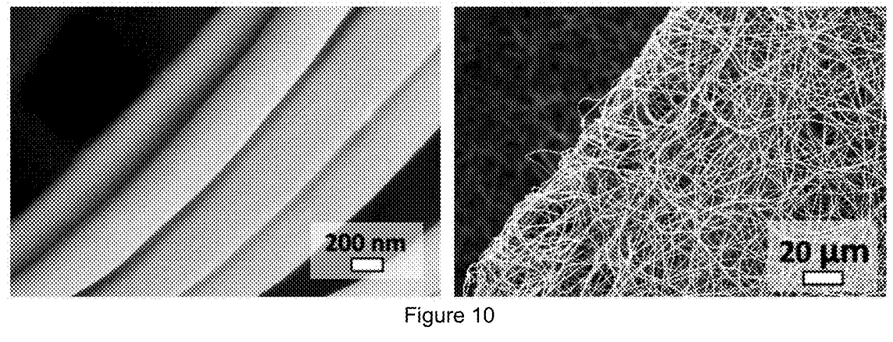
FIG. 10 provides the micro-(left) and macroscale (right) morphology of 99.7 wt % PANi-HCSA with 0.3 wt % PEO nanofibrous non-woven fabric, as observed via SEM imaging.
Figure 11:
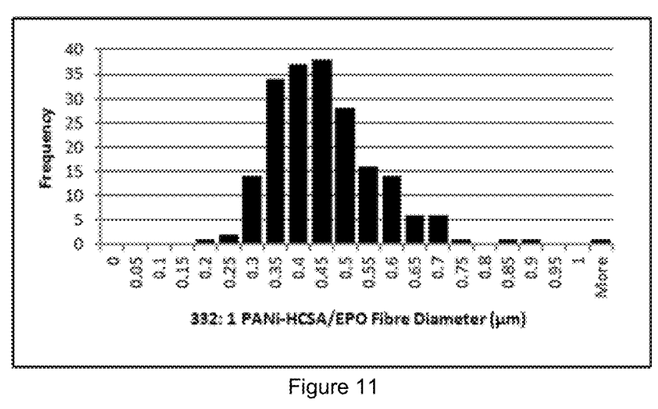
FIG. 11 are graphs illustrating the fibre diameter of 99.7 wt % 65,000 Da (g/mol) PANi-HCSA/0.3 wt % 600,000 Da (g/mol) PEO nanofibres made using a 3:1 DMF/CB solvent system.

UV-visible spectroscopy was used to confirm the production of a PANi-ES solution, PANi-HCSA, in its desirable polaron (as opposed to bipolaron) lattice (see FIGS. 6 and 7).

The broad intraband peak beginning at 520 nm and continuing past 1,000 nm has been associated with the delocalization of electrons. This is opposed to a narrow peak at 800 nm, which is caused by a transition from $\pi$ to a localized polaron band (i.e. $\pi^*$). This $\pi$-$\pi^*$ transition is associated with compact coil conformation of the polymer backbone, which reduces packing efficiency in the bulk product. Poor chain packing reduces the crystallinity of the material, which in turn negativity impacts conductivity.

The inventors believe that morpholine may produce an expanded PANi-EB chain that persists even after morpholine is eliminated via distillation from the system prior to doping. This is evidenced by the lack of cross-linking or self-association induced after morpholine removal, which are both associated with a dramatic decrease in solubility. It is speculated that DMF is able to fully solvate the polymer once an expanded chain conformation has been conferred by the morpholine/imine site interaction.

It is believed that use of the gel inhibitor morpholine causes a persistent and beneficial change in chain conformation prior to doping.

Expanded chain conformation may assist with efficient dissolution, and also may enhance the properties of PANi-ES, which is advantageous in processing methods such as electrospinning.

It is likely that the dissolution in the presence of the gel inhibitor achieves a high level of polymer chain entanglement in solution, which facilitates electrospinning.

Fibre Formation

The PANi-ES solution was subject to electrospinning (e.g. single nozzle electrospinning) to form the PANi-ES fibres.

Single nozzle electrospinning provides a fully automated method of forming continuous nanofibres (up to several metres). A typical electrospinning rig involves the application of a high voltage electrostatic field to a droplet of polymer solution (see FIG. 21).

Figure 21:
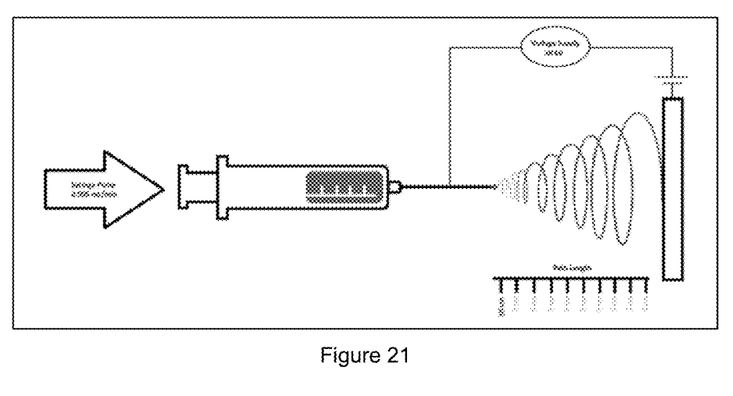
FIG. 21 is an illustration of a single nozzle electrospinning rig.

The applied electric force on the solution's free charges (i.e. ions and electrons) overcomes the surface tension of the droplet, causing a jet to be ejected. As the drift velocity of the free charges propels the jet from the point of eruption (i.e. the Taylor cone) towards a grounded collector, the solvent evaporates and the polymer precipitates into fibres of nanoscale diameter.

An alternative electrospinning method is co-axial electrospinning (also known as co-electrospinning). This technique involves electrospinning two polymer solutions simultaneously to produce core-shell nanostructures; a material physically encapsulated by the shell of a separate material. A co-axial rig comprises a two-compartment pressurized 'polymer bath', which releases separate polymers solution through an aligned outer and inner concentric opening (see FIG. 22).

Figure 22:
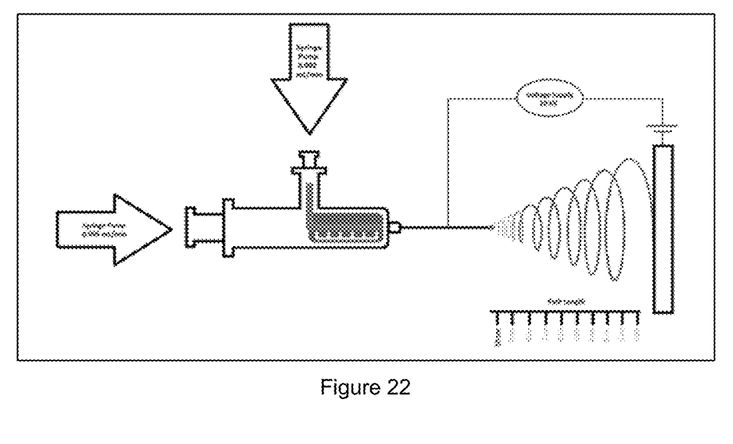
FIG. 22 is an illustration of a co-axial electrospinning rig.

A heterogeneous droplet will form at the opening and transform from the Taylor cone to a deposited fibre via the application of a high voltage electric field. The high speed at which this process takes place generally prevents any mixing of the separate polymer solutions. The benefit of using two polymers simultaneously is that a higher molecular weight polymer shell can be used as a 'carrier' for a low molecular weight polymer 'core' by providing a template that discourages deformation.

Chain entanglement is necessary for the fibre production by electrospinning: the elongation of a polymer solution jet as it travels or elongates through the influence of an electric field. The solvent evaporates during the whipping stage and deposits the jet as solid fibres with diameters in the micro- or nanoscale.

Example 1 provides reaction conditions for the formation of PANi-HCSA solution for fibre formation.

Example 1

A 1:1 DMF/morpholine solution containing 13 wt % 65,000 Da (g/mol) PANi-EB and 0.04 wt % 600,000 Da (g/mol) PEO was heated to 80° C. for 10 minutes with mechanical agitation.

Once fully dissolved, the solution was heated to 130° C. until the total mass of the system was reduced by 75% of the initial value. The solvent volume was replenished with chlorobenzene to produce a 2:1 DMF/chlorobenzene solvent system.

In one embodiment, a 2 mL solution of 1:1 DMF/morpholine typically requires half the DMF volume to be removed in order to effectively remove the morpholine (i.e. a total volume of 1.5 mL of the solvent mixture is typically removed). The reaction mixture is subsequently topped up with a DMF/chlorinated solution to result with a 2:1 or 3:1 DMF/chlorinated solvent system.

Figure 4:
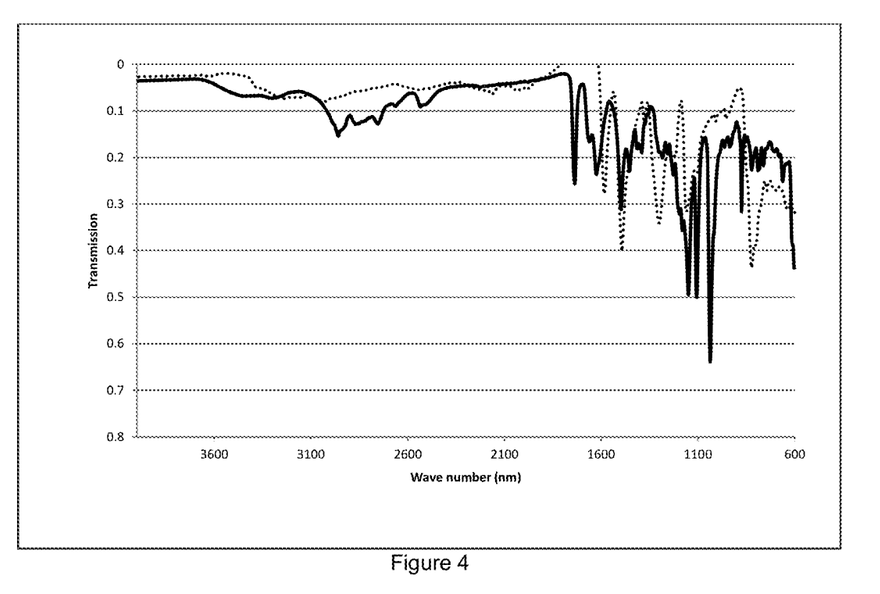
FIG. 4 is a ATR FTIR spectrum of PANi-HCSA film (solid line) after morpholine distillation and PANi-EB stock powder (broken line), which shows peak wavenumber ($cm^{-1}$) value and intensity of all functional groups of polyaniline.

The inventors discovered that in a 1:1 DMF/morpholine solution, cross-linking was observed to occur above 80° C. if the solution is not fully dissolved. However, once morpholine likely occupies the imine sites, the solution can be heated to 130° C. with no observable change in colour or formation of insoluble material. It is postulated that morpholine protects the reactive imine sites, which protects against heat-induced degradation. This stability to heating was supported by FTIR analysis, which shows the persistence of benzenoid and quinoid group stretching by their known peak wavelength in both heat-treated PANi-HCSA film and the untreated solid PANi-EB powder (see FIG. 4 and Table 1).

TABLE 1 the approximate peak intensity of ATR FTIR peaks associated with characteristic functional groups of both PANi-EB and PANi-HCSA, with hydrogen bond shifts in peak maxima taken into consideration.

| Group associated with vibration | Wavenumber (cm$^{-1}$) | PANi-EB Intensity | PANi-HCSA intensity |
|---|---|---|---|
| Benzoid C=C Stretch | ~1590 | 0.272 | 0.225 |
| Quinoid C=C Stretch | ~1500 | 0.395 | 0.305 |
| C—N Stretch | ~1290 | 0.333 | 0.365 |
| N=Q=N Stretch | ~1150 | 0.309 | 0.196 |

The only significant difference between the two spectra that may not be accounted for by acid doping is the disappearance of a broad water peak at 3,100 cm$^{-1}$ after distillation. The presence of water in the stock is not surprising due to PANi-EB's hygroscopic properties.

Therefore, the exploitation of boiling point differences for effective elimination of morpholine is feasible in a PANi-EB solution as long as complete dissolution is achieved first.

Figure 5:
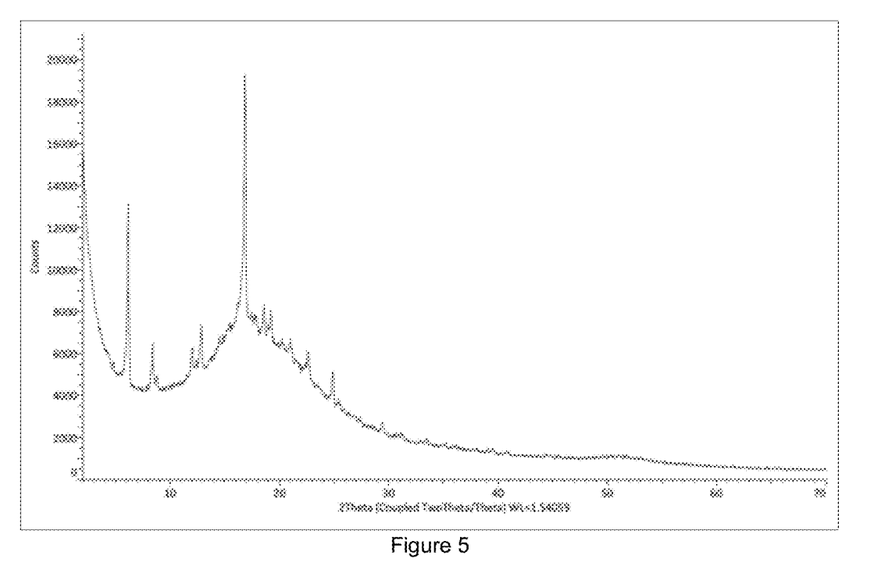
FIG. 5 provides an XRD analysis of a 99.1 wt % PANi-HCSA with 0.9 wt % PEO nanofibrous fabric, showing crystalline peaks in the 2-70° 2Θ of the diffractogram.

Evidence of minimal cross-linking occurring during high temperature dissolution in the presence of morpholine also comes from X-ray Diffraction (XRD) analysis. PANi-HCSA fibres made from distilled solutions exhibit 9% crystallinity (see FIG. 5). This is consistent with literature data on the level of crystallinity expected from non-crosslinked 65,000 Da (g/mol) PANi-ES samples.

It is believed that morpholine dramatically improves the processability of PANi-EB by expanding the polymer chain in a similar way to the process that has been called "secondary doping".

The solution was then cooled and the acid dopant, HCSA, was added to the solution at a 1:1 PANi-EB to HCSA molar ratio. An immediate colour shift from dark blue to a dark green was observed, indicating a doping event.

Solutions between 12-16 wt % 65,000 Da (g/mol) PANi-HCSA prepared in accordance with Example 1 above can be successfully electrospun with 0.3 wt % 600,000 Da (g/mol) PEO using the parameters listed in Table 2.

TABLE 2

Parameters for the electrospinning of a 13 wt % solution of 65,000 Da (g/mol) PANi- HCSA to produce fibres.

| Parameter | Value |
|---|---|
| Voltage | 11 kV |
| Flow rate | 0.005 mL/min |
| Spinneret-collector distance | 15 cm |
| Relative Humidity (RH %) | 40% |

Electrospinning of 12-16 wt % solutions of PANi-HCSA in DMF was achieved by the inclusion of a moderately volatile chlorinated solvent, such as 1,1,2,2-tetrachloroethane (TCE; b.p. 146.7° C.) or chlorobenzene (b.p. 131° C.).

PANi-HCSA fibres formed using single nozzle electrospinning under a variety of conditions as set out in Examples 2 to 4 below.

The formed PANi-HCSA fibres in each of these examples have an average diameter of ranging from 70-10,000 nm.

Example 2

A solution of 99.7% 65,000 Da (g/mol) PANi-HCSA/ 0.3% 600,000 PEO solution in a DMF/CB solvent system was prepared. It was determined that a solvent ratio of 3:1 DMF/CB gave homogeneous fibres with good morphology (see FIGS. 8 to 11).

| Parameter | Value |
|---|---|
| DMF volume | 1.5 mL |
| CB volume | 0.5 mL |
| PANi-EB (wt % in solution) | 13 wt % |
| PANi-EB Mw | 65,000 Da (g/mol) |
| PEO (wt % in solution) | 0.04 wt % |
| PEO Mw | 600,000 Da (g/mol) |
| Voltage | 11 kV |
| Flow path | 10 cm |
| Flow rate | 0.005 mL/min |
| Needle Gauge | 21 G |

Example 3

A solution of 20 wt % 100,000 Da (g/mol) PANi-HCSA in DMAC was made from a solution of 20 wt % PANi-EB in a 1:5 morpholine/DMAC solvent mixture with the morpholine distilled out before electrospinning. The PANi-HCSA solution successfully produced nanofibers using following electrospinning parameters:

TABLE 3 the electrospinning parameters for the production of 100% PANi-HCSA from a DMAC solution

| Parameter | Value |
|---|---|
| DMAC volume | 2 mL |
| PANi-HCSA (wt % in solution) | 20 wt % |
| PANi-EB Mw | 100,000 Da (g/mol) |
| Voltage | 28 kV |
| Flow path | 10 cm |
| Flow rate | 0.005 mL/min |
| Needle Gauge | 18 G |
| Ionic additive | 0.01% 1-butyl-3-methylimidazolium tetrafluoroborate (BMIM) |

Figure 12:
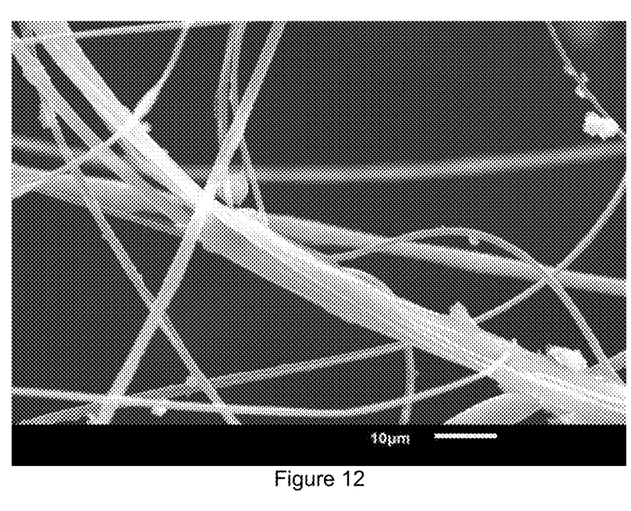
FIG. 12 is a SEM image of 100 wt % PANi-HCSA nanofibers dry electrospun from a DMAC solvent system.
Figure 13:
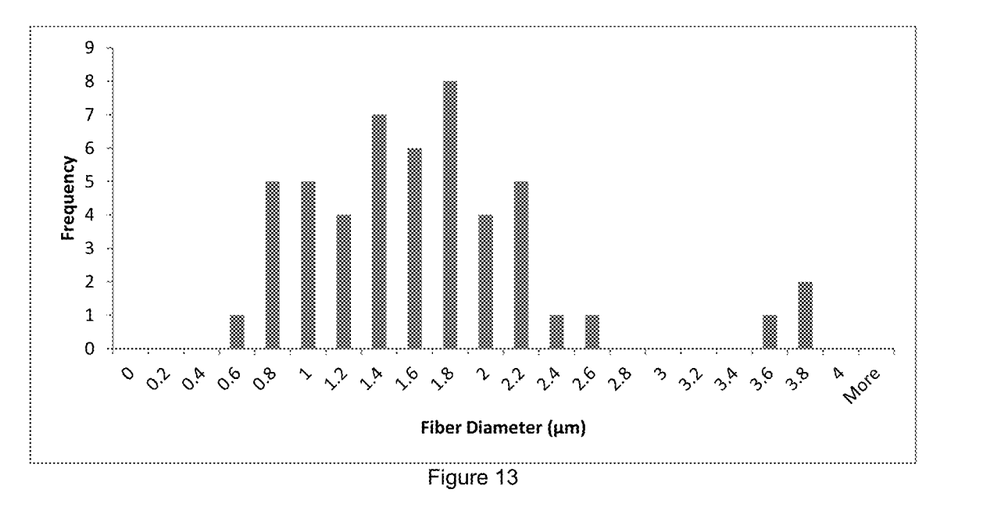
FIG. 13 is a graph illustrating the range of fibers diameters obtained when electrospinning 100 wt % 100,000 Da (g/mol) PANi-HCSA, made from a PANi-EB solution in 1:5 morpholine/DMAC with the morpholine distilled off before doping and electrospinning.

FIG. 12 is a SEM image of 100 wt % PANi-HCSA nanofibers dry electrospun from a PANi-EB solution dissolved in 1:5 morpholine/DMAC solvent system with the morpholine subsequently distilled before doping and electrospinning. The production of nanoscale fibers was confirmed by measuring the diameter of the fibers using SEM imagery and image J software (see FIG. 13).

Example 4

A solution of 99:1 65,000 Da (g/mol) PANi-HCSA/600,000 Da (g/mol) PEO in 1:1 TCE/DMF was successfully electrospun using the following electrospinning parameters:

TABLE 4 the electrospinning parameters for the production of 99:1 PANi-HCSA/PEO in 1:1 TCE/DMF solution

| Parameter | Value |
| --- | --- |
| DMF volume | 1 mL |
| TCE volume | 1 mL |
| PANi-EB (wt % in solution) | 8 wt % |
| PANi-EB Mw | 65,000 Da (g/mol) |
| PEO (wt % in solution) | 0.08 wt % |
| PEO Mw | 600,000 Da (g/mol) |
| Voltage | 10 kV |
| Flow path | 10 cm |
| Flow rate | 0.01 mL/min |
| Needle Gauge | 21 G |
| Ionic additive | 0.01% BMIM |

Figure 14:
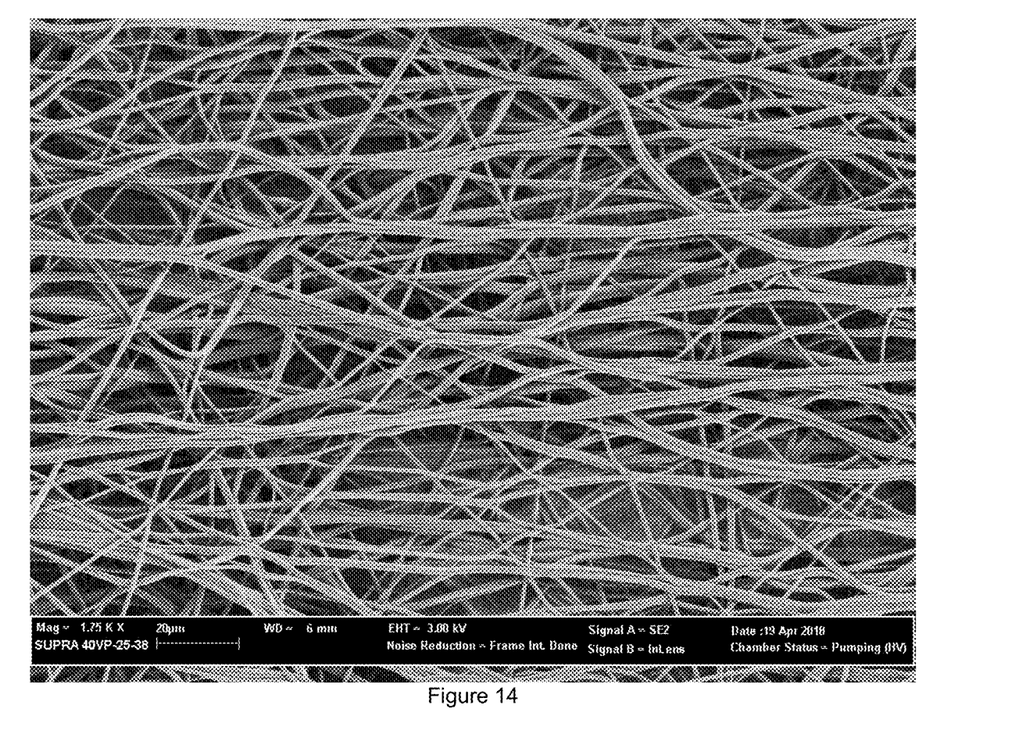
FIG. 14 is a SEM image of 99:1 65,000 Da (g/mol) PANi-HCSA/600,000 Da (g/mol) PEO nanofibers from a solution of 1:1 TCE/DMF, which shows the surface morphology of the fibers.

This solution produced a large quantity of nanoscale fibers that are readily handled as a robust membrane (see FIG. 14).

Figure 15:
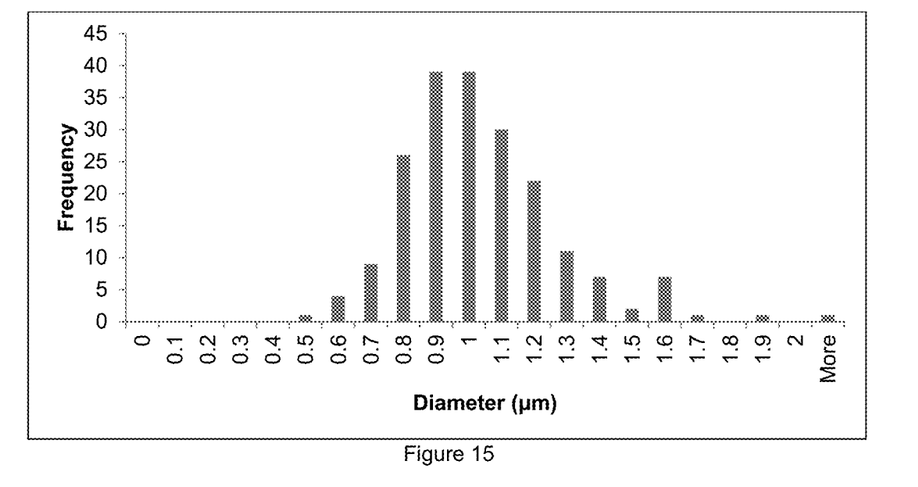
FIG. 15 is a graph illustrating the range of fibers diameters obtained when electrospinning 99:1 65,000 Da (g/mol) PANi-HCSA/600,000 Da (g/mol) PEO from a solution of 1:1 TCE/DMF.

The production of nanoscale fibers was also confirmed by measuring the diameter of the fibers using SEM imagery and image J software (see FIG. 15).

Fibre Fabric Formation

The PANi-HCSA fibres can be formed into a non-woven fabric in accordance with an embodiment of the fifth aspect of the invention.

Figure 16:
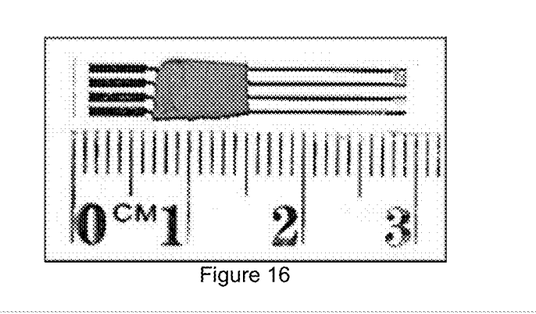
FIG. 16 is an image of a 99:1 PANi-HCSA/PEO sample loaded on a gold electrode array, which is used to make bulk conductivity measurements.

The conductivity and resistivity of the fibre fabric was characterized. Conductivity measurements were taken by loading a sample of PANi-HCSA non-woven fibre fabric onto a gold electrode array printed on to a sitall substrate (see FIG. 16). The conductivity was measured on a 2-point probe multimeter, which was connected to the gold array at varying probe distances.

The following volume resistivity equation was used to calculate the material's bulk conductivity, see Equation 1.

$$\rho_m = \frac{(R_f - R_0)wt}{L}$$

Equation 1: Volume resistivity ($\rho_m$) of the nanofibrous fabric was determined as a function of $R_f$ (measure resistivity), Ro (contact resistance), w (width of the sample), t (thickness of the sample) and L (length between electrode) Fabric resistivity values were measured by a two probe multimeter in contact with two electrodes at a constant distance (L=0.07 cm). Contact resistance (Ro) was determined by plotting the resistivity of the material across the three electrode distances of the interdigitated gold array.

The porosity of the nanofibrous membrane was accounted for by multiplying the resulting bulk conductivity by its porosity ($\phi$), see Equation 2 and 3.

$$\phi = 1 - \frac{\rho_{bulk}}{\rho_{particle}}$$

Equation 2: the porosity of a nanofibrous fabric as a function of the density of the material bulk density ($\rho_{bulk}$) and the known particle density ($\rho_{particle}$)

$$\sigma_f = \frac{1}{\sigma_m} \times \frac{1}{(1 - \phi)}$$

Equation 3: the conductivity of the nanofibres ($\sigma_f$) as a function of fabric conductivity ($\sigma_m$) and porosity ($\phi$)

The resulting conductivity of the a non-woven fibre fabric prepared by electrospinning a solution of 99:1 PANi-HCSA/PEO in 3:1 DMF/chlorobenzene solution showed a bulk conductivity of 0.001 S·cm$^{-1}$.

Gas Sensor

Figure 17:
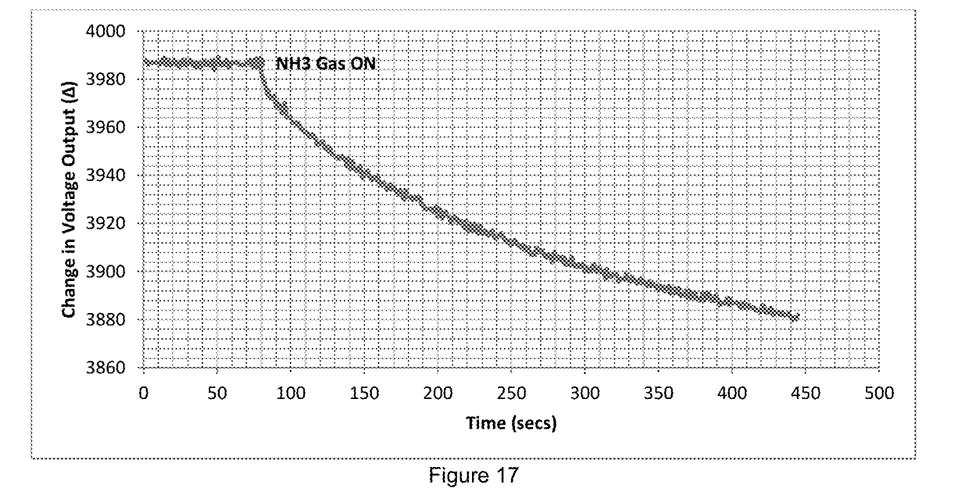
FIG. 17 is a graph illustrating the optical change (photodiode voltage) generated by a PANi-HCSA electrospun fabric on exposure to 50 ppm ammonia flowing at 0.5 L/min.

According to an embodiment of the sixth aspect of the invention, the fibre fabric was exposed to 50 ppm ammonia to determine its ability to detect the gas. An example would be to use this material for OH&S monitoring applications. FIG. 17 illustrates the optical change generated by a PANi-HCSA electrospun fabric on exposure to 50 ppm ammonia (which is the maximum permissible exposure level (PEL) for ammonia) flowing at 0.5 L/min. The response was recorded by a sensing device which measures the reflectance change of a colorimetric reaction and converts this to a voltage output. This change is the green conductive PANi-HCSA fabric dedoping and simultaneously turning into its blue semi-conductive PANi-EB form due to ammonia exposure.

Figure 18:
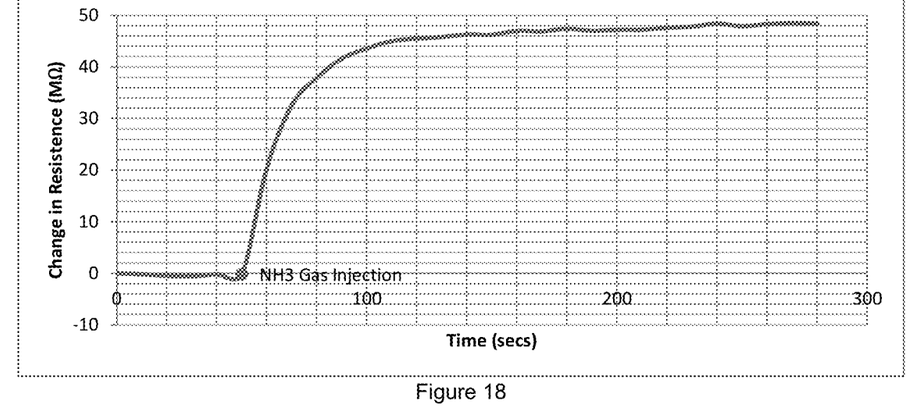
FIG. 18 is a graph illustrating the change in resistivity of a PANi-HCSA fibre fabric exposed to 50 ppm ammonia.

FIG. 18 is a graph illustrating the magnitude of the change in resistivity of a PANi-HCSA fibre fabric to 50 ppm of ammonia. The graph represents a dedoping reaction caused by the presence of ammonia, which lowers the conductivity of the bulk material.

Figure 19:
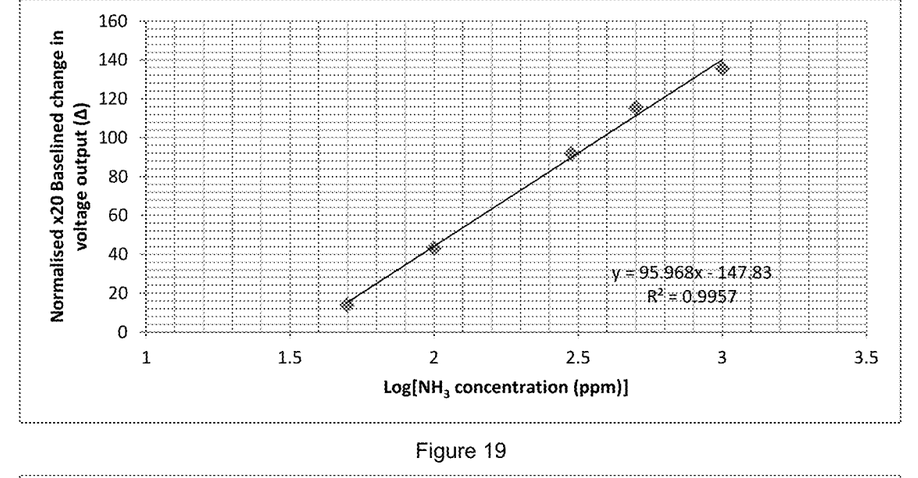
FIG. 19 is a graph illustrating the optical change (photodiode voltage) of a PANi-HCSA fibre fabric to a range of ammonia concentrations.

FIG. 19 is a graph illustrating the change in photodiode voltage caused by the colour change of a PANi-HCSA fibre fabric when exposed to ammonia concentrations ranging from 50 to 1,000 ppm.

These results indicate that the fabric is suitable to be used in a gas sensor for testing for the presence of gaseous substances, by measurement of either its change in colour or electrical properties.

Figure 20:
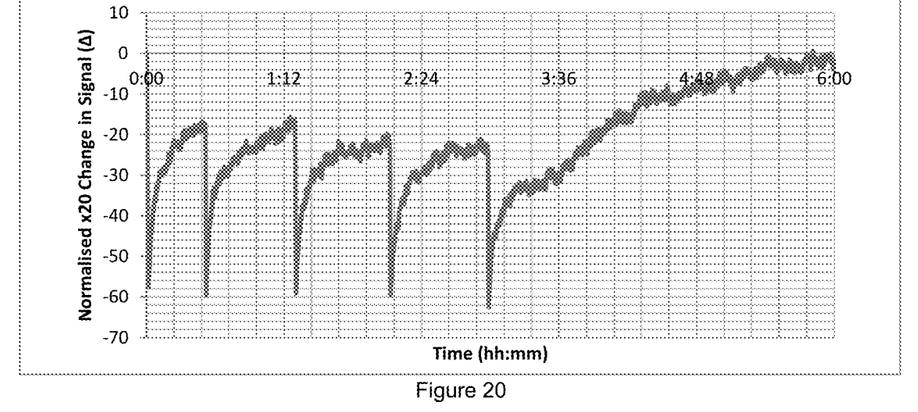
FIG. 20 is a graph illustrating the optical response of PANi-HCSA mats to repeated injections of 100 ppm ammonia in ambient air.

This colour change has been shown to be reversible and reproducible, with five exposures of 100 ppm ammonia using the same PANi-HCSA fabric sensing element resulting in a repeatable colour change measurement that exhibited a 3% relative standard deviation (RHS) (FIG. 20). At the time, the gas sensing elements were a month old; this suggests the PANi-HCSA sensing elements exhibit good longevity.

As such, the present invention provides a process of forming a PANi-ES solution which can be used to form PANi-ES fibres without the need for post synthetic processing of the fibres. It was also demonstrated that a fabric made from the PANi-ES fibres has the ability to detect gases such as ammonia, which makes the fabric suitable for use in a gas sensor.

EXPERIMENTAL

The materials and instrumentation used for the examples are described below.

Materials

The 65,000 Da (g/mol) PANi-EB, (+)-camphor-10-sulfonic acid (HCSA), N,N-dimethylformamide (DMF), 600,000 Da (g/mol) polyethylene oxide (PEO), morpholine, chlorobenzene (CB), and 1,1,2,2-tetrachloroethane were all purchased from Sigma Aldrich.

Instrumentation

The single nozzle dry electrospinning rig and rotating collector were made in-house at the DST Group.

Full color optical images of solutions were taken with an Olympus BH-2 microscope attached to an Olympus 72D camera, which ran on CellSens software.

SEM images were taken with a Hitachi 3030 benchtop SEM and Zeiss SUPRA 40V-25-38, and analyzed using Image-j software for fibre diameter.

The ATR FTIR build for chemical structure analysis was a Thermofisher Nicolet 6700.

Conductivity measurements were made using gold electrode (IDEs) arrays from Nano SPR with a 0.07 cm electrode spacing and sitall substrate. The electrospun fabric thickness measurements required for accurate processing of the conductivity data were performed on a Leica SP5 confocal microscope.

The crystallinity of the PANi-HCSA material was determined using a Rigaku SmartLab X-ray Diffractometer, equipped with a Hi-Pix 3000 detector, which operated in a parallel beam mode under Cu-Kα radiation (45 kV, 200 mA).

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method of forming an acid-doped polyaniline (emeraldine salt) (PANi-ES) solution including steps of:
   (i) mixing polyaniline (emeraldine base) (PANi-EB) with a PANi-EB solvent and a gel-inhibitor to form a gel-inhibited PANi-EB solution;
   (ii) removing the gel-inhibitor from the gel-inhibited PANi-EB solution to form a PANi-EB solution; and
   (iii) adding an acid dopant to the PANi-EB solution to form a PANi-ES solution.

2. The method according to claim 1, wherein the gel inhibitor has a basic pH.

3. The method according to claim 1, wherein the gel-inhibitor has a lower boiling point to the PANi-EB solvent.

4. The method according to claim 1, wherein the PANi-EB solvent is an aprotic solvent.

5. The method according to claim 1, wherein the acid dopant is an organic acid.

6. The method according to claim 1, wherein the PANi-ES solution has a concentration of at least 0.01 wt % PANi-ES.

7. The method according to claim 1, wherein step (i) includes mixing PANi-EB with a PANi-EB solvent and a gel-inhibitor such that the PANi-EB solvent to gel-inhibitor ratio ranges from 1:1 to 1:20.

8. The method according to claim 1, wherein step (i) includes a step of adding a carrier polymer.

9. The method according to claim 1, wherein step (ii) includes removing the gel-inhibitor from the gel-inhibited PANi-EB solution by distillation.

10. The method according to claim 1, wherein step (iii) includes adding an acid dopant to the PANi-EB solution such that the molecular ratio of PANi-EB to acid dopant ranges from 2:1 to 1:2.

11. The method according to claim 1, including a step of adding an organic solvent to the PANi-ES solution.

12. The method according to claim 11, the organic solvent is chlorinated.

* * * * *